United States Patent
Limonadi

(10) Patent No.: US 6,852,067 B2
(45) Date of Patent: Feb. 8, 2005

(54) SYSTEMS FOR THE PREVENTION OR TREATMENT OF CARPAL TUNNEL SYNDROME

(76) Inventor: Farhad M. Limonadi, 13070 SW. 63rd Ave., Portland, OR (US) 97219

( * ) Notice: Subject to any disclaimer, the term of this patent is extended or adjusted under 35 U.S.C. 154(b) by 0 days.

(21) Appl. No.: 10/182,850
(22) PCT Filed: Feb. 9, 2001
(86) PCT No.: PCT/US01/04138
§ 371 (c)(1),
(2), (4) Date: Aug. 1, 2002
(87) PCT Pub. No.: WO01/58538
PCT Pub. Date: Aug. 16, 2001

(65) Prior Publication Data
US 2003/0013580 A1 Jan. 16, 2003

Related U.S. Application Data

(60) Provisional application No. 60/242,092, filed on Oct. 23, 2000, provisional application No. 60/181,899, filed on Feb. 11, 2000, and provisional application No. 60/181,210, filed on Feb. 9, 2000.

(51) Int. Cl.[7] .............................................. G01H 11/00
(52) U.S. Cl. ........................ 482/8; 473/213; 400/704; 601/33
(58) Field of Search .............................. 473/213; 482/1, 482/4, 8, 3, 900; 400/703, 704; 601/23, 33

(56) References Cited

U.S. PATENT DOCUMENTS

| | | | |
|---|---|---|---|
| 5,286,244 A | | 2/1994 | Wright et al. |
| 5,335,918 A | | 8/1994 | Rupnik et al. |
| 5,743,805 A | | 4/1998 | Richter |
| 5,823,886 A | * | 10/1998 | Murray ........................ 473/213 |
| 5,868,632 A | * | 2/1999 | Drelick ........................ 473/213 |
| 5,876,292 A | * | 3/1999 | Hamilton ..................... 473/213 |
| 5,895,326 A | * | 4/1999 | Cozza et al. ................. 473/213 |

* cited by examiner

Primary Examiner—Glenn E. Richman
(74) Attorney, Agent, or Firm—Klarquist Sparkman, LLP

(57) ABSTRACT

Apparatuses and methods for preventing and/or treating carpal tunnel syndrome are disclosed. One such apparatus comprises a splint for wearing on a portion of an upper extremity of an individual, a warning mechanism carried by the splint and a switch mechanism carried by the splint and electrically coupled to the warning mechanism. The switch mechanism is operable to activate the warning mechanism upon extension or flexion of the hand beyond a predetermined range of motion and thereby alert the user of such undesirable motion of the hand.

25 Claims, 4 Drawing Sheets

SYSTEMS FOR THE PREVENTION OR TREATMENT OF CARPAL TUNNEL SYNDROME

CROSS-REFERENCE TO RELATED APPLICATIONS

This is the National Stage of International Application No. PCT/US01/04138, filed Feb. 9, 2001, and claims the benefit of U.S. Provisional Application No. 60/242,092, filed Oct. 23, 2000, U.S. Provisional Application No. 60/181,899, filed Feb. 11, 2000, and U.S. Provisional Application No. 60/181,210, filed Feb. 9, 2000.

FIELD

The present invention relates to preventing and treating hand disorders, and more particularly, to preventing and treating carpal tunnel syndrome.

BACKGROUND

Carpal tunnel syndrome is a nerve disorder in the hand that is caused by swollen, inflamed or scarred tissue as well as repetitive or excessive motion injuries that cause excessive pressure on the median nerve within the carpal tunnel. The median nerve supplies sensation to the volar, also known as the plamar, aspect of the thumb, index finger, middle finger and the ring finger. Symptoms of carpal tunnel syndrome include tingling, numbness, burning sensations, pain. This involves not only the area of innervation described but may also radiate above the wrist into the forearm. An individual with carpal tunnel syndrome may also experience stiffness or cramping of hands, and may loss the ability to grasp objects or operate certain devices commonly used in the individual's household or workplace.

Treatment for carpal tunnel syndrome has included rest from provocative activities, anti-inflammatory medications, steroid injections, surgery, and/or the use of wrist splints to fix the wrist in either a neutral or extended position. While these measures may control symptoms temporarily, they have proven to be less successful in permanently controlling or relieving symptoms.

Surgery may offer a more permanent control of symptoms, however, there is a period of temporary disability following surgery. Also, there are inherent risks with any surgical procedure. In addition, it has been proven to be an expensive method of treatment. Lastly, there is a possibility of symptoms returning when one resumes their pre-surgical activities and in some cases more severe symptoms may develop due to post-surgical scar formation in the carpal tunnel.

Neutral or extended wrist splints have provided control of symptoms for some people during sleeping hours. However, use of these splints during waking hours has proven to be impractical for most people due to the rigid immobilization of the wrist and partial immobilization of the base of the thumb that these splints create, in view of the degree of flexion and extension that may be required for performing certain tasks. In fact, such restricted range of motion of the wrist and thumb may aggravate carpal tunnel syndrome due to the abnormal manner in which the fingers and thumb would be forced to function while wearing the splint. In addition, a wearer is likely to cause excessive pressure on the limb from positioning the arm or wrist in an abnormal manner to compensate for the lack of mobility. Consequently, the rigid portions of a splint transfers the excessive pressure, typically at the distal and proximal ends of the splint, to the adjacent portions of the limb, thereby causing pain or numbness in those portions. Also, prolonged use of a wrist splint may cause muscle atrophy or wasting.

Further, wrist splints are disadvantageous in that they do not assist the patient in changing or modifying the behavior (e.g., hyperextension or hyperflexion) that is causing the trauma responsible for carpal tunnel syndrome. In fact, it is likely that the patient will continue to apply excessive pressure on the affected limb, which may keep him dependent on using the splint at nights to prevent worsening of his symptoms.

Thus, a need exists for apparatuses and methods for treating and preventing carpal tunnel syndrome that overcome the disadvantages of the prior art.

SUMMARY

According to one aspect, an apparatus for preventing and treating carpal tunnel syndrome comprises a splint for wearing on a portion of an upper extremity of an individual, a switch mechanism connected to the splint and a warning mechanism electrically coupled to the switch mechanism. The switch mechanism is operable to activate the warning mechanism upon extension or flexion of the hand beyond a predetermined range of motion and thereby alert the user of such undesirable motion of the hand. By alerting the user as to when undesirable hyperflexion or hyperextension is occurring, the user will be able to modify behavior accordingly so as to eliminate the excessive pressure being applied to the wrist and causing the trauma responsible for carpal tunnel syndrome.

In one exemplary embodiment, the splint comprises a forearm portion pivotally coupled to a hand portion so as to define a pivot axis coinciding with the extension and flexion axis of the hand to permit extension and flexion of the hand. A multi-level rotary switch is operatively connected to the forearm portion and the hand portion and operable to activate the warning mechanism if the motion of the hand exceeds a predetermined, threshold set by user. A microcontroller may be electrically connected to the rotary switch for recording the amount, duration, and frequency of the flexion and extension of the hand. This information can be downloaded to a computer where it can be analyzed. Such information can be used to determine the etiology of carpal tunnel syndrome for a particular patient. The forearm portion of the splint may comprise a proximal portion coupled to a distal portion in such a manner so as to permit radial and ulnar motion of the hand. The splint may also include a selectively lockable pivot joint to mechanically limit the allowable extension and flexion of the hand.

In another embodiment, a switch mechanism carried by a splint is operable to generate a radio signal to activate a remote mounted alarm.

A method for preventing and treating carpal tunnel syndrome in an individual comprises detecting information motions of the hand of the individual and immediately notifying the individual of detected motions responsible for carpal tunnel syndrome.

It is therefore a principal object of the present invention to provide a way to prevent or relieve the symptoms of carpal tunnel syndrome.

DETAILED DESCRIPTION

Figure 1:
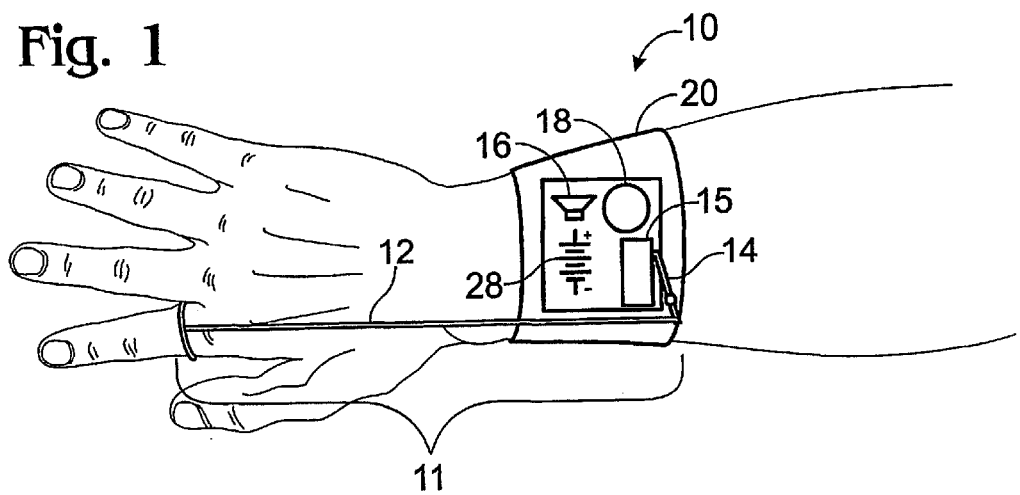
FIG. 1 is a schematic plan view of the dorsal side of an apparatus for treating carpal tunnel syndrome installed on a right upper extremity.

Referring to FIG. 1, there is shown an apparatus 10 for preventing and treating carpal tunnel syndrome installed on the right upper extremity of a patient. The apparatus 10 in the form shown includes a switch mechanism 11 comprising a lever 14 of a microswitch 15 and a flexible string or cord 12, such as an elastomeric band, on the dorsal side of the hand. The distal end of the cord 12 is secured to the index finger in the form shown and coupled to the lever 14 at the other end. Alternatively, the distal end of the cord may be secured to any suitable point on the dorsal side of the hand. The lever 14 is positioned proximally of the wrist of the wearer (as viewed in FIG. 1) and carried by or otherwise mounted to a suitable splint or other mounting device adapted to be worn on the patient. In the illustrated embodiment, the splint comprises a band or wrap 20 secured to the forearm of the wearer. The lever 14 is electrically connected to one or more conventional warning mechanisms, such as an audible alarm 16 and vibrating motor 18, which are also carried by or otherwise mounted to the wrap 20. Also, the warning mechanism may comprise a warning light A selector switch (not shown) may be provided to allow the wearer to use either the alarm 16, vibrating motor 18, or both. A battery 28 is electrically connected to the microswitch 15, alarm 16 and vibrating motor 18 to power the apparatus 10.

Upon excessive flexion of the hand, the cord 12 moves the lever 14 distally (i.e., towards the fingertips) to complete an electrical circuit, thereby activating the warning mechanism and alerting the wearer that he or she has hyperflexed the wrist beyond a predetermined range of motion. By alerting the wearer as to when undesirable hyperflexion is occurring, he will be able to modify his behavior so as to eliminate the excessive pressure being applied to the wrist and causing carpal tunnel syndrome.

The apparatus 10 may include a second flexible cord (not shown) on the palmar side of the hand to detect excessive extension of the wrist. In such a case, the second cord is secured at one end to the proximal portion of the finger and coupled to the lever 14 at the other end. Thus, upon excessive extension of the wrist, the second cord moves the lever 14 proximally (i.e., away from the fingertips) to complete the electrical circuit, thereby activating the warning mechanism and alerting the wearer that he or she has hyperextended the wrist beyond a predetermined range of motion. In another modification of the present embodiment, the apparatus 10 may be provided with a flexible cord to detect excessive extension and the cord 12 for detecting excessive flexion, such as shown in FIG. 1, could be eliminated. In all cases, however, the amount of extension or flexion required before a warning mechanism is activated can be varied by adjusting the length of the appropriate cord.

Figure 2:
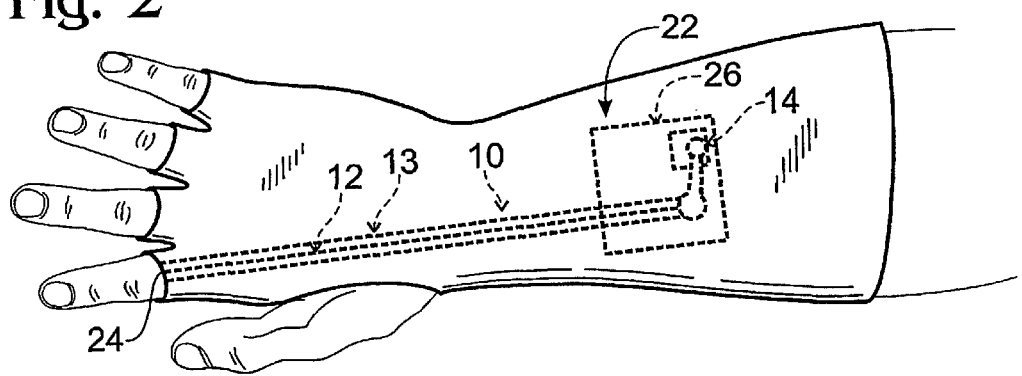
FIG. 2 is a perspective view of the apparatus of FIG. 1 showing the apparatus integrated with a splint installed on the right upper extremity.

As shown in FIG. 2, the apparatus 10 may be integrated with a splint 22, preferably made of a flexible fabric like material, for wearing on the hand and forearm. In this embodiment, one end of a cord 12 is secured to the dorsal side of the splint 22 at 24. The cord 12 extends through an internal sleeve 13 sewn into the splint 22 and is coupled at its other end to the lever 14. The lever 14 and the electrical components (e.g., alarm, vibrating motor, battery) of the apparatus 10 may be secured within a pocket 26 sewn into the splint 22. A second cord (not shown) may be provided in a similar manner on the palmer side of the sleeve 22.

Figure 1A:
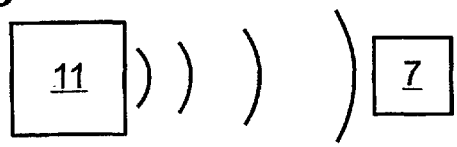
FIG. 1A is a schematic view of a remote mounted alarm mechanism for the apparatus of FIG. 1.

In a modification to the apparatus of FIGS. 1 and 2, the switch mechanism 11 is operable to generate a radio signal to activate a remote mounted alarm mechanism 7 (as shown in FIG. 1A).

Figure 3:
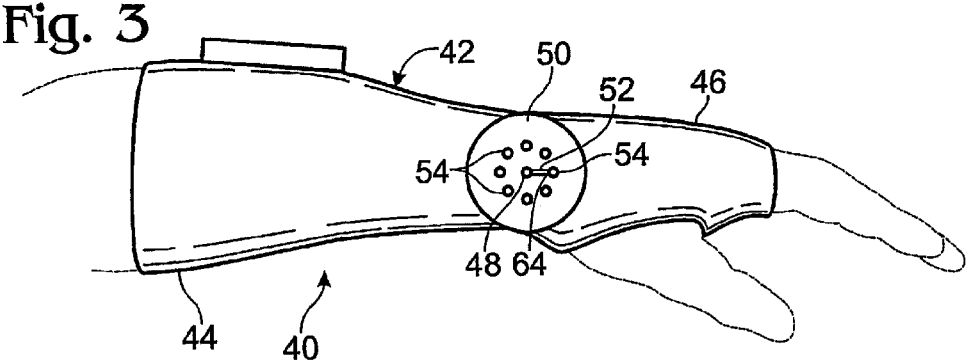
FIG. 3 is a schematic side view of another apparatus for treating carpal tunnel syndrome.
Figure 7:
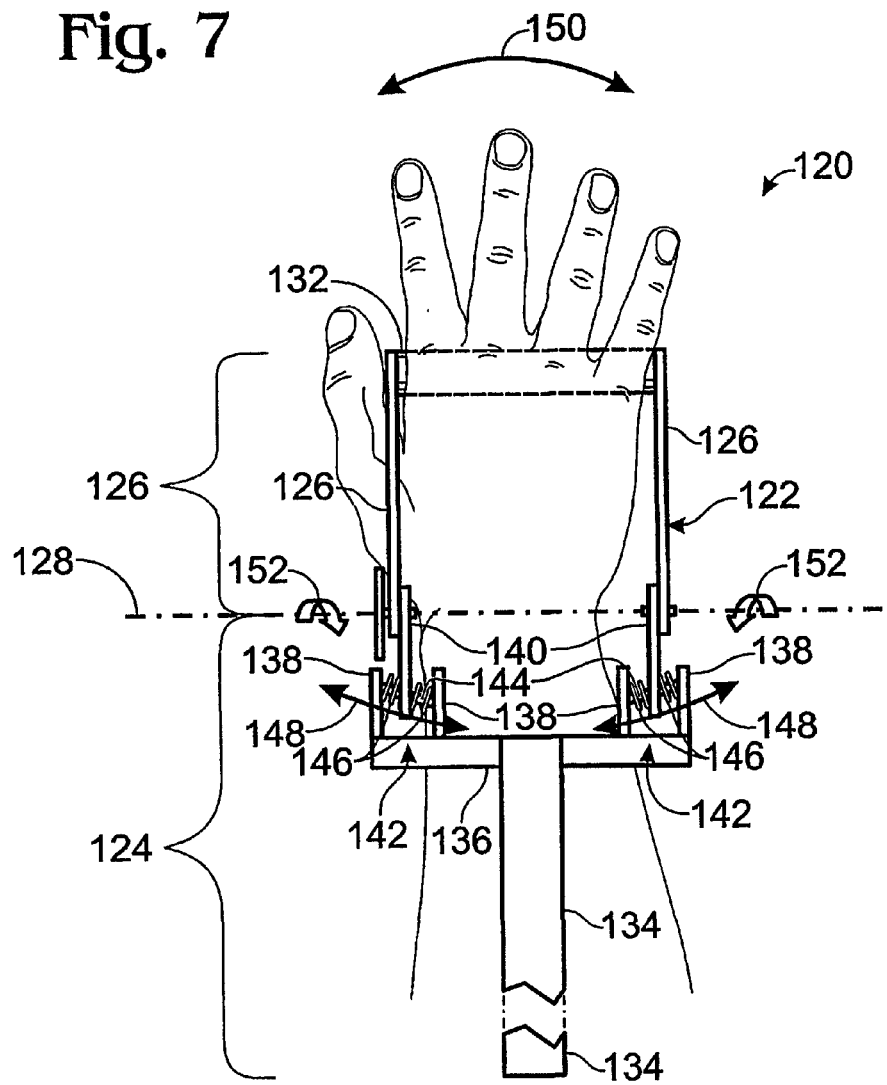
FIG. 7 is a schematic plan view of the dorsal side of another apparatus for treating carpal tunnel syndrome installed on a right upper extremity.

Referring to FIG. 3, there is shown another apparatus 40 for preventing and treating carpal tunnel syndrome. The apparatus 40 comprises a splint 42 for wearing on an affected upper extremity. The splint 42 includes a forearm piece 44 pivotally coupled to a hand piece 46 so as to define a pivot axis at 48 extending generally perpendicular to the plane of the page bearing FIG. 3. Consequently, when the splint is installed on an upper extremity, the pivot axis is generally coincident with the extension and flexion axis of the wrist to permit extension or flexion of the hand/hand piece 46. In one form, the forearm piece 44 and hand piece 46 of the splint 42 are each made of a flexible fabric like material having integral, rigid braces extending along the sides thereof, wherein the braces of the hand piece and forearm piece on each side are pivotally coupled at their adjacent ends (as shown in FIG. 7 without a fabric covering).

A multi-position rotary switch 50 is operatively connected to the forearm piece 44 and the hand piece 46 at the pivot axis. The rotary switch 50 includes a rotatable element 52 having fixed end at 48 and a free end 64 for electrically contacting a plurality of circumferentially spaced contacts 54. Element 52 is operable to rotate about the pivot axis upon extension or flexion of the hand/hand piece 46. Accordingly, the free end 64 will electrically contact the contacts 54, each of which corresponds to a different position of the hand/hand piece 46, as the hand/hand piece 46 pivots about the pivot axis.

Figure 4:
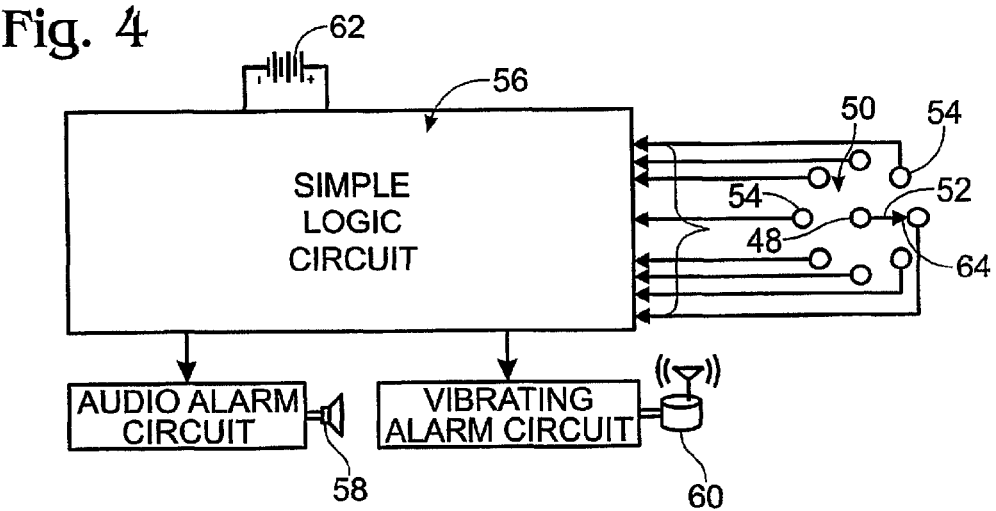
FIG. 4 is a schematic of an electrical feedback system for the apparatus of FIG. 2.

Referring to FIG. 4, there is shown an electrical feedback system to alert the user should any hyperextension or hyperflexion occur. The feedback system comprises a logic circuit 56 electrically connected to each of the contacts 54. Electrically connected to the logic circuit 56 is an audible alarm 58, a vibrating motor 60, and a battery 62. Other types of warning mechanisms, such as a warning light, may also be used. A selector switch (not shown) may be provided to allow the wearer to use either the alarm 16, vibrating motor 18, or both. These components are carried by or otherwise mounted to the splint 42 in any suitable manner.

The logic circuit 56 includes a user input pin (not shown), which allows the user to set the rotary switch 50 to activate either the alarm 16 or the vibrating motor 18 for at least two positions of the hand/band piece 46 (i.e., at two of the contacts 54). Thus, the user can define a predetermined range of motion for extension and flexion of the hand beyond which one of the warning mechanisms (whichever one is selected by the user) will alert the user of such excessive extension and flexion. In a working embodiment, red and green warning lights are electrically connected to the circuit 56 wherein the green light is illuminated if the hand is within the predetermined range of motion and the red light is illuminated if the hand is beyond the predetermined range of motion.

In a modification to the apparatus 40 of FIGS. 3 and 4, a rotary potentiometer can be used in lieu of a multi-position rotary switch to achieve the same effect of the rotary switch.

Figure 5:
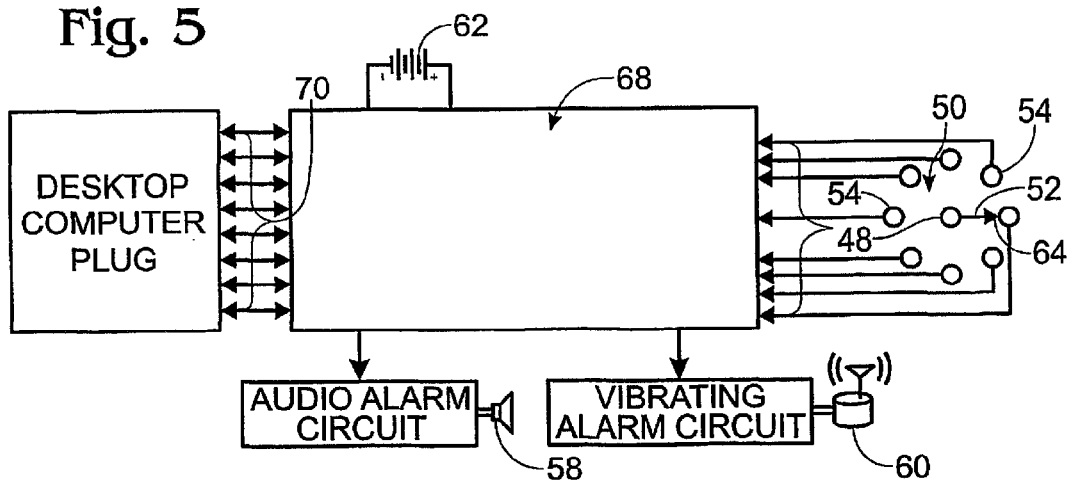
FIG. 5 is a schematic of another electrical feedback system for the apparatus of FIG. 2.

As shown in FIG. 5, the logic circuit 56 of FIG. 4 can be replaced with a microcontroller 68 having a computer readable medium for measuring and recording the amount, duration, and frequency of the flexion and extension of the hand and other useful information as a function of time and date. The microcontroller 68 has input/output lines 70 to download the recorded information to a desktop or laptop computer where the information can be reviewed and analyzed by the user and/or the user's doctor. Such information will enable the user to determine which tasks or activities put the user at risk for prolonged, or excessive hyperextension or hyperflexion that cause the trauma responsible for carpal tunnel syndrome.

Figure 6A:
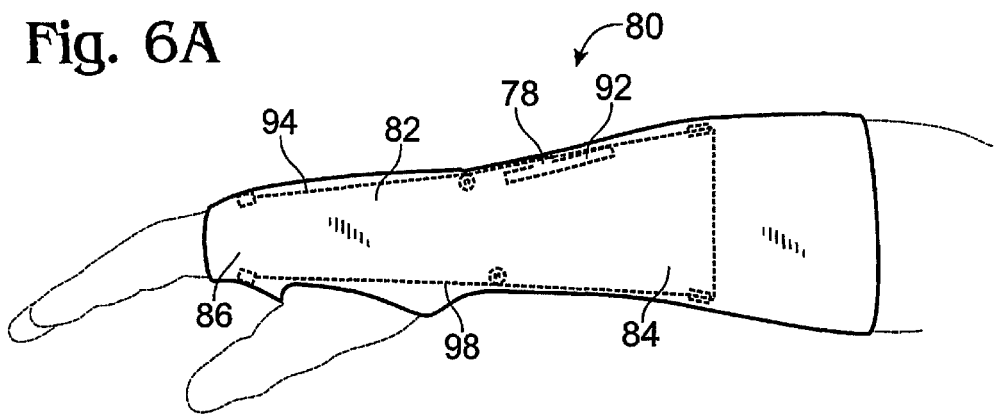
FIG. 6A is a schematic side view of another apparatus for treating carpal tunnel syndrome.
Figure 6B:
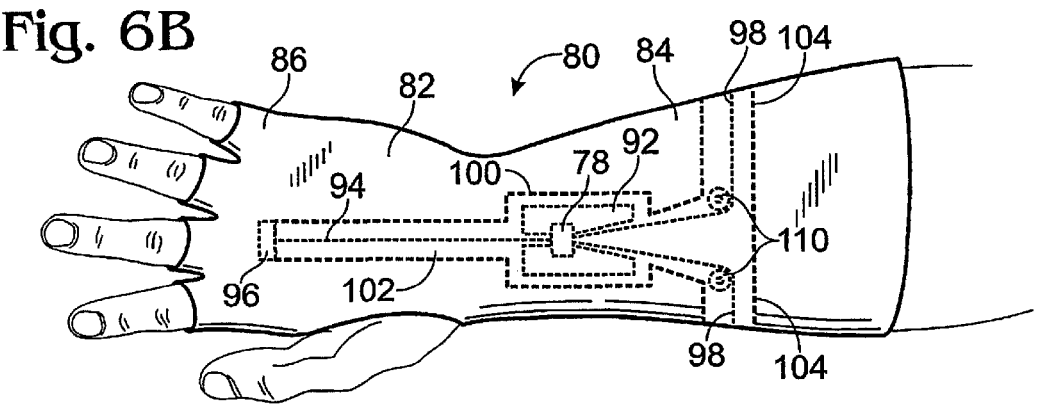
FIG. 6B is a schematic plan view of the dorsal side of the apparatus of FIG. 6A installed on a right upper extremity.
Figure 6C:
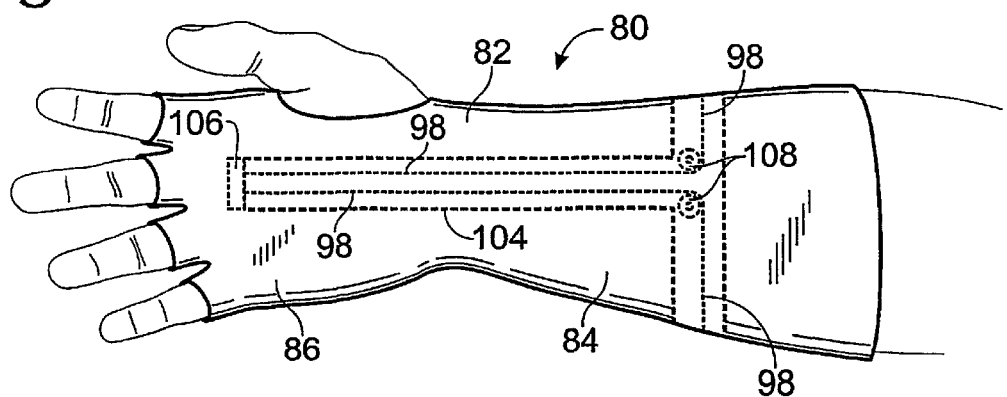
FIG. 6C is a schematic plan view of the palmar side of the apparatus of FIG. 6B.

FIGS. 6A–6C illustrate another apparatus 80, which comprises a splint 82 for wearing on an upper extremity. In the illustrated embodiment, the splint 82 comprises a flexible, one-piece construction having a hand portion 86 for covering the hand and a forearm portion 84 for covering the forearm. Such a construction for the splint 82 is advantageous in that rigid braces which would otherwise prevent ulnar and radial motion of the hand are not required.

The apparatus 80 includes a switch mechanism for detecting excessive extension or flexion. The switch mechanism comprises a multi-position linear switch 92 operatively connected to a dorsal cord 94 (FIG. 6B) and two palmar cords 98 (FIG. 6C). In a modification of the present embodiment, a linear potentiometer may be used in lieu of the linear switch 92 to achieve the same effect of the lever switch.

The linear switch 92 is carried by or otherwise mounted to the dorsal side of the forearm portion 84. In the illustrated form, the linear switch 92 is contained in a sleeve or pocket 100 sewn into the forearm portion 84 (FIG. 6B). Alternatively, the linear switch may be positioned in a similar manner on the palmar side of the forearm portion 84, in which case there would be two dorsal cords and a single palmar cord. In either case, the linear switch 92 is electrically connected to an electrical feedback system, such as previously described with respect to the rotary switch 50 of FIG. 4, to detect and alert the user of any hyperextension or hyperflexion. Like the rotary switch 50, the linear switch 92 is a multi-position switch which allows the user to define a predetermined range of motion by inputting the levels at which an alarm mechanism is to be activated. If desired, the microcontroller 68 of FIG. 5 may be used to record information relating to the motion of the hand.

As best shown in FIG. 6B, the dorsal cord 94 extends through a sleeve 102 sewn into the dorsal side of the forearm portion 84 and hand portion 86. The distal end of the cord 94 is connected to a slide contact 78 of the linear switch 92 and its proximal end is connected to the hand portion 86 at 96. As shown in FIG. 6C, each palmar cord 98 is secured to the palmar side of the hand portion 86 at 106 and extends to the distal end portion of the forearm portion 84, at which point each cord 98 is reeved around a pin 108. Each cord 98 is further reeved around a pin 110 on the dorsal side of the forearm portion and then connected to the slide contact 78 of the linear switch 92 (FIG. 6B). Also, as shown in FIGS. 6B and 6C, each cord 98 extends through a sleeve 104 sewn into the forearm portion 84 and hand portion 86.

The apparatus 80 operates in the following manner. The slide 78 of the switch 92 is pulled distally (i.e., towards the fingertips) by the dorsal cord 94 upon flexion of the hand. Conversely, the slide 78 of the switch 92 is pulled proximally (i.e., away from the finger tips) by the palmar cords 98 upon extension of the hand. If the amount of extension or flexion is beyond the predetermined range of motion, the switch 92 activates an alarm mechanism to alert the user of the excessive extension or flexion.

Referring now to FIG. 7, there is shown an apparatus 120 according to another embodiment of the invention. The apparatus 120 includes a splint 122 having a forearm portion 124 and a hand portion 126. The hand portion 126 has two longitudinally extending side braces 126 connected by a transverse brace 132. The forearm portion 124 comprises two longitudinally extending side braces 140, the distal ends of which are pivotally connected to the proximal ends of the side braces 126 of the hand portion 126 so as to define a pivot axis 128 generally coincident with the extension and flexion axis of the wrist. As such, the splint 122 allows for extension and flexion of the hand/hand portion 126 about axis 128. The proximal ends of the side braces 140 of the forearm portion 124 are coupled, as described below, to the ends of a transverse brace 136 at joints 142 so as to permit ulnar and radial motion of the hand. Connected to the transverse brace 136 is a main longitudinal brace 134.

Each joint 142 of the forearm portion 124 comprises a pair of spaced apart extensions 138 connected to one end of the transverse brace 136. An arcuate retaining pin 144 extends through an aperture in the proximal end of each side brace 140 and is secured at each end to an extension 138. The pin 144 of each joint 142 extends through a pair of springs 146 to center and stabilize the side brace 140 between the extensions 138 while permitting sliding of the side brace 140 relative to the pin 144 (as indicated by arrows 148) so as to enable ulnar and radial motion of the hand/hand piece 126 (as indicated by double-headed arrow 150).

Figure 8:
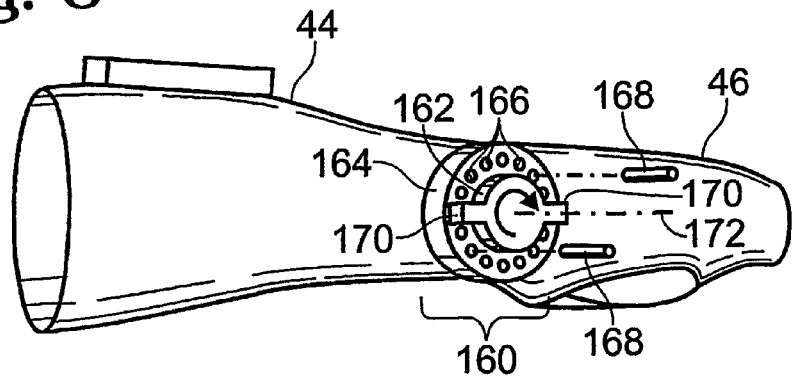
FIG. 8 is a schematic perspective view of another apparatus for treating carpal tunnel syndrome showing a selectively lockable pivot joint.

Referring to FIG. 8, there is shown a selectively lockable pivot joint 160 according to another embodiment for mechanically limiting the allowable extension and flexion of the hand piece relative to the forearm piece of a splint. The adjustable pivot joint 160 can, for example, be used with the splint 42 of FIG. 3 or splint 122 of FIG. 7. In one embodiment, the joint 160 includes an inner cylinder 162 having two diametrically opposed extensions 170 and mounted, for example, to the hand piece of a splint. A concentric outer cylinder 164, which can be mounted to the forearm piece of the splint, has a plurality of circumferentially spaced apertures 166 for receiving locking pins 168. Consequently, extension and flexion of the hand will cause rotation of the inner cylinder 162 relative to the outer cylinder 164 about an axis of rotation 172. The rotation of the inner cylinder 162, and therefore the allowable extension and flexion of the hand, is limited by the pins 168 inserted into any of the apertures 166. Other equivalent structures could be used to mechanically limit the extension and flexion of the hand piece.

Devices are shown and described for illustrative purposes only. The present invention may be subject to many modifications and changes without departing from the spirit or essential characteristics thereof. I therefore claim as my invention all such modifications as come within the spirit and scope of the following claims.

I claim:

1. An apparatus for preventing or treating carpal tunnel syndrome comprising:
   a splint for wearing on a portion of an upper extremity of an individual;
   a switch mechanism connected to the splint; and
   a warning mechanism electrically coupled to the switch mechanism, the switch mechanism being operable to activate the warning mechanism upon extension of the hand beyond a first predetermined threshold of a range of motion and upon flexion of the hand beyond a second predetermined threshold of the range of motion.

2. The apparatus of claim 1 wherein the splint comprises a forearm portion pivotally connected to a hand portion with the hand portion being adapted to rotate about a pivot axis located to generally coincide with the extension and flexion axis of the wrist of the individual when the apparatus is worn.

3. The apparatus of claim 2 wherein the switch mechanism comprises a multi-position rotary switch operatively connected to the forearm portion and the hand portion and operable to activate the warning mechanism if the motion of the hand exceeds the first predetermined threshold or the second predetermined threshold.

4. The apparatus of claim 2 wherein the switch mechanism comprises a rotary potentiometer operatively connected to the forearm portion and the hand portion and operable to activate the warning mechanism if the motion of the hand exceeds the first predetermined threshold or the second predetermined threshold.

5. The apparatus of claim 1 wherein the warning mechanism comprises an audible alarm.

6. The apparatus of claim 1 wherein the warning mechanism comprises a vibrating motor.

7. The apparatus of claim 1 wherein the warning mechanism comprises at least one warning light.

8. The apparatus of claim 1 wherein the switch mechanism is carried by the splint.

9. The apparatus of claim 1 wherein the warning mechanism is carried by the splint.

10. The apparatus of claim 8 wherein the warning mechanism is carried by the splint.

11. An apparatus for preventing or treating carpal tunnel syndrome comprising:
    a splint for wearing on a portion of an upper extremity of an individual;
    a switch mechanism connected to the splint, and
    a warning mechanism electrically coupled to the switch mechanism, the switch mechanism being operable to activate the warning mechanism upon extension or flexion of the hand beyond a predetermined range of motion:
    wherein the switch mechanism comprises:
    a lever mounted on the splint adjacent the forearm of the upper extremity;
    a cord having first and second ends, the first end connected to the lever and a second end for securing to a portion of the hand of the upper extremity wherein motion of the hand pulls the cord, thereby causing the lever to move and activate the warning mechanism if the motion of the hand exceeds a predetermined threshold.

12. The apparatus of claim 1 wherein the splint comprises a flexible one-piece construction having a hand portion and a forearm portion.

13. The apparatus of claim 12 wherein the switch mechanism comprises:
    a lever mounted on the forearm portion of the splint; and
    at least a first cord and a second cord, the first cord having first and second ends, the first end of the first cord connected to the lever and the second end of the first cord connected to the hand portion wherein extension of the hand pulls the first cord, thereby causing the lever to move and activate the warning mechanism if the hand is extended beyond the first predetermined threshold, the second cord having first and second ends, the first end of the second cord connected to the lever and the second end of the second cord connected to the hand portion wherein flexion of the hand pulls the second cord, thereby causing the lever to move and activate the warning mechanism if the hand is flexed beyond the second predetermined threshold.

14. An apparatus for preventing or treating carpal tunnel syndrome comprising:
    a splint for wearing on a portion of an upper extremity of an individual;
    a switch mechanism connected to the splint; and
    a warning mechanism electrically coupled to the switch mechanism, the switch mechanism being operable to activate the warning mechanism upon extension or flexion of the hand beyond a predetermined range of motion;
    wherein the switch mechanism comprises:
    a multi-position linear switch mounted on the forearm portion of the splint; and
    at least one cord having first and second ends, the first end connected to the linear switch and a second end connected to the hand portion wherein motion of the hand pulls the cord, thereby causing the linear switch to move and activate the warning mechanism if the motion of the hand exceeds a predetermined threshold.

15. An apparatus for preventing or treating carpal tunnel syndrome comprising:
    a splint for wearing on a portion of an upper extremity of an individual;
    a switch mechanism connected to the splint;
    a warning mechanism electrically coupled to the switch mechanism, the switch mechanism being operable to activate the warning mechanism upon extension or flexion of the hand beyond a predetermined range of motion; and
    a microcontroller electrically connected to the switch mechanism and including a memory for storing information relating to the extension and flexion of the hand.

16. The apparatus of claim 2 wherein the forearm portion comprises a proximal portion and a distal portion coupled to the proximal portion, wherein the distal portion is movable relative to the proximal portion in the radial and ulnar directions so as to permit radial and ulnar motion of the hand.

17. A method for preventing or treating carpal tunnel syndrome in an individual comprising:
    detecting motions of the hand of the individual, wherein detecting motions of the hand comprises detecting extension of the hand beyond a first predetermined threshold and detecting flexion of the hand beyond a second predetermined threshold; and immediately notifying the individual of detected motions responsible for carpal tunnel syndrome.

18. A method for preventing or treating carpal tunnel syndrome in an individual comprising:

detecting motions of the hand of the individual; immediately notifying the individual of detected motions of the type responsible for carpal tunnel syndrome: and storing information relating to the motion of the hand on a computer readable medium.

19. The method of claim 17 wherein immediately notifying the individual of detected motions responsible for carpal tunnel syndrome comprises activating an alarm when the motion of the hand exceeds a predetermined threshold.

20. An apparatus for preventing or treating carpal tunnel syndrome comprising:

a splint for wearing on a portion of an upper extremity of an individual, the splint having a forearm portion pivotally connected to a hand portion with the hand portion being adapted to rotate about a pivot axis located to generally coincide with the extension and flexion axis of the wrist of the individual when the apparatus is worn, the forearm portion having a proximal portion coupled to a distal portion in such a manner so as to permit radial and ulnar motion of the hand;

a warning mechanism mounted on the splint;

a multi-position rotary switch operatively connected to the forearm portion and the hand portion and electrically coupled to the warning mechanism, wherein the switch is operable to activate the warning mechanism if the motion of the hand exceeds a predetermined threshold; and a selectively lockable pivot joint for limiting the range of motion for extension and flexion of the hand.

21. An apparatus for preventing or treating carpal tunnel syndrome comprising:

a splint for wearing on a portion of an upper extremity of an individual;

a switch mechanism connected to the splint; and a warning mechanism electrically coupled to the switch mechanism the switch mechanism being operable to activate the warning mechanism upon extension or flexion of the hand beyond a predetermined range of motion;

wherein the switch mechanism comprises:

a potentiometer mounted on the forearm portion of the splint; and at least one cord having first and second ends, the first end connected to the potentiometer and a second end connected to the hand portion wherein motion of the hand pulls the cord, thereby causing the potentiometer to move and activate the warning mechanism if the motion of the hand exceeds a predetermined threshold.

22. The apparatus of claim 16, wherein the forearm portion is configured to permit limited motion of the hand in the radial and ulnar directions.

23. An apparatus for preventing or treating carpal tunnel syndrome comprising:

a switch mechanism operable to detect extension or flexion of a hand beyond a predetermined range of motion;

a mounting device adapted for wearing on a portion of an upper extremity of an individual, wherein the switch mechanism is mounted to the mounting device; and a microcontroller electrically connected to the switch mechanism and including a memory for storing information relating to the extension and flexion of the hand.

24. A method for preventing or treating carpal tunnel syndrome in an individual comprising:

detecting motions of the hand of the individual;

storing information relating to the motion of the hand on a computer readable medium; and identifying activities that involve hand motions that cause carpal tunnel syndrome based on the information stored on the computer readable medium.

25. The method of claim 24, wherein storing information relating to the motion of the hand comprises storing the type of each motion that is detected and the time at which each motion is detected.

* * * * *

UNITED STATES PATENT AND TRADEMARK OFFICE
CERTIFICATE OF CORRECTION

PATENT NO. : 6,852,067 B2
APPLICATION NO. : 10/182850
DATED : February 8, 2005
INVENTOR(S) : Farhad M. Limonadi It is certified that error appears in the above-identified patent and that said Letters Patent is hereby corrected as shown below:

Column 1, line 33, "loss" should be --lose--.
Column 2, line 39, "predetermined," should be --predetermined--.
Column 3, line 48, "light A" should be --light. A--.
Column 5, line 2, "the hand/band piece" should be --the hand/hand piece--.
Column 7, line 56, "motion:" should be --motion;--.
Column 9, line 7, "syndrome:" should be --syndrome;--.

Signed and Sealed this

Nineteenth Day of December, 2006

JON W. DUDAS
*Director of the United States Patent and Trademark Office*